US005454973A

United States Patent [19]

Koseki et al.

[11] Patent Number: 5,454,973

[45] Date of Patent: Oct. 3, 1995

[54] STABLE DISPERSIBLE MINERAL ACID SLURRY OF BENZIDINE DERIVATIVES

[75] Inventors: Fumio Koseki; Kenjiro Fujiki; Motonori Takeda; Katsutoshi Tao, all of Wakayama, Japan

[73] Assignee: Wakayama Seika Kogyo Co., Ltd., Wakayama, Japan

[21] Appl. No.: 136,025

[22] Filed: Oct. 14, 1993

[30] Foreign Application Priority Data

Oct. 16, 1992 [JP] Japan .................................... 4-278278

[51] Int. Cl.[6] ....................................................... C09K 3/00

[52] U.S. Cl. .................... 252/182.12; 252/311; 106/499; 536/52; 536/60; 536/114; 536/123.1; 564/5

[58] Field of Search .............................. 252/182.12, 311; 106/499; 536/52, 60, 114, 123.1; 564/5

[56] References Cited

U.S. PATENT DOCUMENTS

| | | | |
|---|---|---|---|
| 4,556,640 | 12/1985 | Gantzer | 436/66 |
| 4,559,160 | 12/1985 | Schultz | 252/182.12 |
| 4,613,631 | 9/1986 | Espenscheid et al. | 523/130 |

FOREIGN PATENT DOCUMENTS 64-42456 2/1989 Japan .

*Primary Examiner*—Shailendra Kumar

*Attorney, Agent, or Firm*—Wenderoth, Lind & Ponack

[57] ABSTRACT

Mineral acid slurries of benzidine derivatives having high stability are provided by incorporating into such slurries a polysaccharide.

27 Claims, No Drawings

STABLE DISPERSIBLE MINERAL ACID SLURRY OF BENZIDINE DERIVATIVES

BACKGROUND OF THE INVENTION

The present invention relates to a mineral acid slurry of a benzidine derivative having high stability in which the benzidine derivative is suspended in a dilute mineral acid.

Benzidine derivatives constitute the primary disazo components used in the production of dyes and also yellow, orange and blue diszo pigments applied for printing ink and plastics. 3,3'-Dichloro-4,4'-diaminobiphenyl, which is representative of the benzidine derivatives, is suspected as a cancer causing agent throughout the world and various regulations for its handling are established in various countries.

3,3'-Dichloro-4,4'-diaminobiphenyl, 3,3'-dimethoxy-4,4'-diaminobiphenyl and 3,3'-dimethyl-4,4'-diaminobiphenyl are listed on the group-1 substances in the laws on prevention of hazards due to specified chemical substances of the industrial safety and health laws in Japan. For the manufacture and handling of them, it is required that employees wear proper protective clothing, that they be handled in a closed system, that they be supplied as a wet product and that a local ventilation system be provided for decontamination. These protections are necessary in order to avoid human exposure to these materials.

Under the regulations, a benzidine derivative as a product is shipped generally in the form of a wet powder containing water or acid to avoid raising dust.

However, as the above method, i.e., the wet powder form, is not a complete solution to the problem of dust and there remains a possibility that operators might be exposed to the benzidine derivative. In order to decrease human exposure due to dusting of the product, it is necessary to make the benzidine derivative into a slurry form and to transport it in a closed container or a tank lorry, to convey the slurry by pumping and to handle it in an even more closed system.

Further, in the case of a benzidine derivative which is solid at room temperature being made into slurry, the stability of the slurry is important.

As for a method for obtaining a slurry of 3,3'-dichloro-4,4'-diaminobiphenyl having stable dispersibility, for example, U.S. Pat. No. 4,559,160 has proposed specifically defining the hydrochloric acid concentration and the 3,3'-dichloro-4,4'-diaminobiphenyl content in the slurry. Further, in Japanese Laid-open Publication No. Sho. 64-42456, in addition to the definition of the hydrochloric acid concentration and the 3,3'-dichloro-4,4'-diaminobiphenyl content, it has been proposed to add a nonionic surface active agent to the slurry.

In the above two patent publications, the solid component in the slurry, 3,3'-dichloro-4,4'-diaminobiphenyl, partially settles out and is thus separated from its mother liquor, and it solidifies in a few days.

In order to store the slurry, the settled solid must be soft enough to be easily agitated and homogeneously re-dispersed into the slurry. However, in the above two patent publications, the settled solid becomes too hard to be agitated and therefore, there still remains a problem that the slurry needs to be continuously agitated for smooth discharge.

SUMMARY OF THE PRESENT INVENTION

In view of the above problem, an object of the present invention is to provide a slurry of a benzidine derivative having stable dispersibility and which can be homogeneously dispersed by agitation even after sedimentation.

In order to achieve the above object, the present invention provides a mineral acid slurry of a benzidine derivative in which the benzidine derivative is in suspension in dilute mineral acid, and containing at least one kind of polysaccharide.

As for the benzidine derivatives employed in the present invention, while they are not limited, for example, 3,3'-dichloro-4,4'-diaminobiphenyl, 3,3'-dimethoxy-4,4'-diaminobiphenyl or 3,3'-dimethyl-4,4'-diaminobiphenyl, which are listed on the group-1 substances in the laws on prevention of hazards due to specified chemical substances, are preferably utilized. These benzidine derivatives are used in any form, such as free base, mono salt or di-salt. Further, they are made into slurry having stable dispersibility without grinding. However, more stable, homogeneous slurry can be obtained by grinding.

The content of the benzidine derivative based on the free base is preferred to be less than 80 wt %, and more preferably, from 30 to 60 wt %. A content of less than 30 wt % is not economical in view of storage, transport and concentration in application. On the other hand, in case of a content above 60 wt %, there is needed special equipment for the discharge of products because of high viscosity.

Various kinds of polysaccharides can be used in the present invention but preferably, a kind of polysaccharide which acts as a protective colloid even in the strong acid region is used, such as, propylene glycol alginate, agar, carrageenan, Furcellaran, gum arabic, tragacanth gum, calla gum, locust bean gum, cationic guar gum, tara gum, tamarind gum, quince seed gum, pectin polysaccharide, sodium dextran sulfate, cyclodextrin, xanthan gum, succinoglycan, pullulan and cycloamylose. Especially, xanthan gum or succinoglycan is preferred from the point of view of acid resistance.

These kinds of polysaccharides may be added individually or a mixture of two or more kinds of polysaccharide may be added together. The addition of the polysaccharide is preferred to be in an amount of from 0.01 to 5 wt % of the dilute mineral acid, and more preferably, from 0.1 to 1 wt %. The addition of too much polysaccharide may lead to difficulties in effluent treatment or may affect the properties of the dyes and pigments produced therefrom.

As the mineral acid, while not specifically limited, for example, hydrochloric acid, sulfuric acid or phosphoric acid may be effectively used in the present invention. The amount of the mineral acid is preferred to be from 1 to 28 wt %, and more preferably from 10 to 20 wt % based on the total weight of the slurry.

In the above described composition, the benzidine derivatives in the slurry does not separate from the mother liquor to a great extent. Even when sediment does occur, it is easily dispersed by agitation.

DETAILED DESCRIPTION OF PREFERRED EXAMPLES

The present invention is described in the following examples and comparative example. Needless to say, the present invention is not restricted to the examples which are purely illustrative and not exhaustive of the invention.

EXAMPLE 1

First, 140 g of 15% hydrochloric acid is agitated in a 300 ml tall beaker at a rate of 500 rpm, and 1.3 g of propylene glycol alginate is gradually added during agitation and dissolved in one hour.

Next, 157.8 g of 3,3'-dichloro-4,4'-diaminobiphenyl dihydrochloride (free amine purity 73.3 wt %) is added over the period of one hour and agitated for another hour to obtain a 38.9 wt % slurry of 3,3'-dichloro-4,4'-diaminobiphenyl having stable dispersibility. A part of the slurry settled after storage for 18 days but the sediment is so soft as to be easily agitated and homogeneously dispersed into the slurry.

EXAMPLE 2

First, 140 g of 15% hydrochloric acid is agitated in a 300 ml tall beaker at a rate of 500 rpm, and 0.7 g of xanthene gum is gradually added during agitation and dissolved in one hour.

Next, 157.8 g of 3,3'-dichloro-4,4'-diaminobiphenyl dihydrochloride (free amine purity 73.3 wt %) is added over the period of one hour and agitated for another hour to obtain a 38.9 wt % slurry of 3,3'-dichloro-4,4'-diaminobiphenyl having stable dispersibility. A part of the slurry settled after storage for 18 days but the sediment is so soft as to be easily agitated and homogeneously dispersed into the slurry.

Comparative Example 1

In case the propylene glycol alginate is not added in Example 1, a part of the 3,3'-dichloro-4,4'-diaminobiphenyl slurry settles after 3 days. The sediment becomes so hard that it is difficult to agitate it.

EXAMPLE 3

The procedure of Example 1 is followed except that 0.35 g of succinoglycan is added instead of the propylene glycol alginate of Example 1. In this case, sedimentation is hardly seen after storage for 18 days and the sediment is so soft as to be easily agitated and homogeneously dispersed into the slurry.

EXAMPLE 4

The procedure of Example 1 is followed except that 0.18 g of succinoglycan is added instead of the propylene glycol alginate of Example 1. A part of the 3,3'-dichloro-4,4'-diaminobiphenyl slurry settled after storage for 18 days but the sediment is so soft as to be easily agitated and homogeneously dispersed into the slurry.

EXAMPLE 5

The procedure of Example 1 is followed except that 1.4 g of cationic guar gum is added instead of the propylene glycol alginate of Example 1. A part of the 3,3'-dichloro-4,4'-diaminobiphenyl slurry settled after storage for 8 days but the sediment is so soft as to be easily agitated and homogeneously dispersed into the slurry.

EXAMPLE 6

First, 93.33 g of 10% hydrochloric acid is agitated in a 300 ml tall beaker at a rate of 500 rpm, and 0.23 g of succinoglycan is gradually added during agitation and dissolved in one half an hour.

Next, 200.86 g of 3,3'-dichloro-4,4'-diaminobiphenyl dihydrochloride (free amine purity 73.3 wt %) is added over the period of one hour and agitated for another hour to obtain a 50.0 wt % slurry of 3,3'-dichloro-4,4'-diaminobiphenyl having stable dispersibility. In this case, no sedimentation is seen after storage for 10 days and the slurry is soft.

EXAMPLE 7

First, 140 g of 10% hydrochloric acid is agitated in a 300 ml tall beaker at a rate of 500 rpm, and 1.3 g of propylene glycol alginate is gradually added during agitation and dissolved in one hour.

Next, 158.5 g of 3,3'-dimethoxy-4,4'-diaminobiphenyl dihydrochloride (free amine purity 72.5 wt %) is added over the period of one hour and agitated for another hour to obtain a 38.5 wt % slurry of 3,3'-dimethoxy-4,4'-diaminobiphenyl having stable dispersibility. A part of the slurry settled after storage for 18 days but the sediment is so soft as to be easily agitated and homogeneously dispersed into the slurry.

EXAMPLE 8

First, 78.5 g of 10% hydrochloric acid is agitated in a 300 ml tall beaker at a rate of 500 rpm, and 0.19 g of succinoglycan is gradually added during agitation and dissolved in one half an hour.

Next, 211.5 g of 3,3'-dimethyl-4,4'-diaminobiphenyl dihydrochloride (free amine purity 58.04 wt %) is added over the period of one hour and agitated for another hour to obtain a 42.3 wt % slurry of 3,3'-dimethyl-4,4'-diaminobiphenyl having stable dispersibility. A part of the slurry settled after storage for 14 days but the sediment is so soft as to be easily agitated and homogeneously dispersed into the slurry.

EXAMPLE 9

The procedure of Example 2 is followed except that 140 g of 5% sulfuric acid is added instead of the 140 g of 15% hydrochloric acid in Example 2. A part of the 3,3'-dichloro-4,4'-diaminobiphenyl slurry settled after storage for 18 days but the sediment is so soft as to be easily agitated and homogeneously dispersed into the slurry.

EXAMPLE 10

The procedure of Example 2 is followed except that 140 g of 5% phosphoric acid is added instead of the 140 g of 15% hydrochloric acid in Example 2. A part of the 3,3'-dichloro-4,4'-diaminobiphenyl slurry settled after storage for 18 days but the sediment is so soft as to be easily agitated and homogeneously dispersed into the slurry.

EXAMPLE 11

The procedure of Example 2 is followed except that 140 g of 5% hydrochloric acid is added instead of the 140 g of 15% hydrochloric acid in Example 2. A part of the 3,3'-dichloro-4,4'-diaminobiphenyl slurry settled after storage for 18 days but the sediment is so soft as to be easily agitated and homogeneously dispersed into the slurry.

What is claimed is:

1. In a mineral acid slurry of a benzidine derivative wherein a benzidine derivative is suspended in a dilute mineral acid, the improvement wherein there is incorporated into the slurry a stabilizing amount of at least one polysaccharide.

2. A mineral acid slurry of a benzidine derivative as in claim 1, wherein said at least one polysaccharide is selected from the group consisting of propylene glycol alginate, agar, carrageenan, Furcellaran, gum arabic, tragacanth gum, calla gum, locust bean gum, cationic guar gum, tara gum, tamarind gum, quince seed gum, pectin polysaccharide, sodium dextran sulfate, cyclodextrin, xanthan gum, succinoglycan, pullulan and cycloamylose.

3. A mineral acid slurry of a benzidine derivative as in claim 1, wherein the polysaccharide is succinoglycan, xanthan gum or a mixture thereof.

4. A mineral acid slurry of a benzidine derivative as in claim 1, wherein the amount of the polysaccharide is from 0.01 to 5 wt % of the dilute mineral acid.

5. A mineral acid slurry of a benzidine derivative as in claim 2, wherein the amount of the polysaccharide is from 0.01 to 5 wt % of the dilute mineral acid.

6. A mineral acid slurry of a benzidine derivative as in claim 3, wherein the amount of the polysaccharide is from 0.01 to 5 wt % of the dilute mineral acid.

7. A mineral acid slurry of a benzidine derivative as in claim 1, wherein the mineral acid is at least one acid selected from the group consisting of hydrochloric acid, sulfuric acid and phosphoric acid.

8. A mineral acid slurry of a benzidine derivative as in claim 2, wherein the mineral acid is at least one acid selected from the group consisting of hydrochloric acid, sulfuric acid and phosphoric acid.

9. A mineral acid slurry of a benzidine derivative as in claim 3, wherein the mineral acid is at least one acid selected from the group consisting of hydrochloric acid, sulfuric acid and phosphoric acid.

10. A mineral acid slurry of a benzidine derivative as in claim 4, wherein the mineral acid is at least one acid selected from the group consisting of hydrochloric acid, sulfuric acid and phosphoric acid.

11. A mineral acid slurry of a benzidine derivative as in claim 5, wherein the mineral acid is at least one acid selected from the group consisting of hydrochloric acid, sulfuric acid and phosphoric acid.

12. A mineral acid slurry of a benzidine derivative as in claim 6, wherein the mineral acid is at least one acid selected from the group consisting of hydrochloric acid, sulfuric acid and phosphoric acid.

13. A mineral acid slurry of a benzidine derivative as in claim 1, wherein the amount of the mineral acid is from 1 to 28 wt % based on the total weight of the slurry.

14. A mineral acid slurry of a benzidine derivative as in claim 2, wherein the amount of the mineral acid is from 1 to 28 wt % based on the total weight of the slurry.

15. A mineral acid slurry of a benzidine derivative as in claim 3, wherein the amount of the mineral acid is from 1 to 28 wt % based on the total weight of the slurry.

16. A mineral acid slurry of a benzidine derivative as in claim 4, wherein the amount of the mineral acid is from 1 to 28 wt % based on the total weight of the slurry.

17. A mineral acid slurry of a benzidine derivative as in claim 5, wherein the amount of the mineral acid is from 1 to 28 wt % based on the total weight of the slurry.

18. A mineral acid slurry of a benzidine derivative as in claim 6, wherein the amount of the mineral acid is from 1 to 28 wt % based on the total weight of the slurry.

19. A mineral acid slurry of a benzidine derivative as in claim 7, wherein the amount of the mineral acid is from 1 to 28 wt % based on the total weight of the slurry.

20. A mineral acid slurry of a benzidine derivative as in claim 8, wherein the amount of the mineral acid is from 1 to 28 wt % based on the total weight of the slurry.

21. A mineral acid slurry of a benzidine derivative as in claim 9, wherein the amount of the mineral acid is from 1 to 28 wt % based on the total weight of the slurry.

22. A mineral acid slurry of a benzidine derivative as in claim 10, wherein the amount of the mineral acid is from 1 to 28 wt % based on the total weight of the slurry.

23. A mineral acid slurry of a benzidine derivative as in claim 11, wherein the amount of the mineral acid is from 1 to 28 wt % based on the total weight of the slurry.

24. A mineral acid slurry of a benzidine derivative as in claim 12, wherein the amount of the mineral acid is from 1 to 28 wt % based on the total weight of the slurry.

25. A mineral acid slurry of a benzidine derivative as in claim 1 wherein the benzidine derivative is a member selected from the group consisting of 3,3'-dichloro-4,4'-diaminobiphenyl; 3,3'-dimethoxy-4,4'-diaminobiphenyl and 3,3'-dimethyl-4,4'-diaminobiphenyl.

26. A mineral acid slurry of a benzidine derivative as in claim 25 wherein the benzidine derivative is 3,3'-dichloro-4,4'-diaminobiphenyl.

27. A method for improving the stability of a mineral acid slurry of a benzidine derivative in which a benzidine derivative is suspended in a dilute mineral acid, which comprises incorporating into the slurry a stabilizing amount of at least one polysaccharide.

* * * * *